(12) United States Patent
Burton

(10) Patent No.: US 7,552,654 B2
(45) Date of Patent: *Jun. 30, 2009

(54) SOIL SAMPLER APPARATUS AND METHOD

(76) Inventor: James D. Burton, 649 Jackson 917, Newport, AR (US) 72112

( * ) Notice: Subject to any disclaimer, the term of this patent is extended or adjusted under 35 U.S.C. 154(b) by 0 days.

This patent is subject to a terminal disclaimer.

(21) Appl. No.: 11/825,483

(22) Filed: Jul. 6, 2007

(65) Prior Publication Data

US 2007/0256509 A1 Nov. 8, 2007

Related U.S. Application Data

(63) Continuation of application No. 10/548,907, filed as application No. PCT/US2004/007183 on Mar. 9, 2004, now Pat. No. 7,255,016.

(60) Provisional application No. 60/454,460, filed on Mar. 13, 2003.

(51) Int. Cl.
E21B 49/02 (2006.01)
G01N 1/04 (2006.01)

(52) U.S. Cl. .............. 73/864.45; 73/864.32; 73/864.41; 73/864.44; 173/19; 173/24; 173/25; 175/20

(58) Field of Classification Search .................. 73/863, 73/864, 864.31, 864.32, 864.41–864.45; 173/18, 19, 184, 24, 25; 175/20, 162, 246, 175/51, 58, 62, 244
See application file for complete search history.

(56) References Cited

U.S. PATENT DOCUMENTS

| 1,362,968 | A | * | 12/1920 | Stewart | 73/863.41 |
| 2,565,224 | A | * | 8/1951 | Gibbens | 173/40 |
| 3,084,553 | A | * | 4/1963 | Cullinan et al. | 73/864.31 |
| 3,331,249 | A | * | 7/1967 | Boxrud | 73/864.31 |
| 3,464,504 | A | * | 9/1969 | Stange | 173/28 |
| RE30,901 | E | * | 4/1982 | Boxrud | 73/864.31 |
| 4,332,301 | A | * | 6/1982 | Jonell | 175/50 |
| 4,333,541 | A | * | 6/1982 | Doty | 175/162 |
| 4,336,849 | A | * | 6/1982 | Hug | 175/246 |
| 4,356,734 | A | * | 11/1982 | Ivancsics | 73/864.31 |
| 4,869,115 | A | * | 9/1989 | Edwards et al. | 73/864.31 |
| 4,989,678 | A | * | 2/1991 | Thompson | 175/20 |
| 5,076,372 | A | * | 12/1991 | Hellbusch | 175/20 |
| 5,211,248 | A | * | 5/1993 | Nosewicz et al. | 175/20 |
| 5,213,169 | A | * | 5/1993 | Heller | 175/122 |
| 5,394,949 | A | * | 3/1995 | Wright et al. | 175/20 |
| 5,887,491 | A | * | 3/1999 | Monson et al. | 73/864.74 |
| 5,950,741 | A | * | 9/1999 | Wright et al. | 175/20 |

(Continued)

Primary Examiner—David A. Rogers
(74) Attorney, Agent, or Firm—J. Charles Dougherty

(57) ABSTRACT

An apparatus removes soil samples at intervals over a field of interest. The apparatus comprises a sampling assembly (60) that rotates on a track (32) riding on a plurality of idler wheels (29, 31). A probe (66) extends and retracts under the action of a scissored frame assembly (70), mechanically manipulated by passage of the scissored frame assembly (70) along a guide assembly (108). The probe (66) is extended into the ground and retracted on each revolution. An ejector (68) pushes soil from the probe (66) as it passes over a hopper (88) to retain the cores. The cores are pneumatically transferred from the hopper (88) to a plurality of sample collection containers (126). An electronic control system uses GPS location information to deposit collected cores in the appropriate container (126) based upon the current location of the apparatus in the field of interest.

13 Claims, 10 Drawing Sheets

U.S. PATENT DOCUMENTS

| | | | | |
|---|---|---|---|---|
| 6,016,713 | A * | 1/2000 | Hale | 73/864.45 |
| 6,119,531 | A * | 9/2000 | Wendte et al. | 73/863.52 |
| 6,237,429 | B1 * | 5/2001 | Melnyk | 73/864.45 |
| 6,260,633 | B1 * | 7/2001 | Machek et al. | 175/20 |
| 6,360,829 | B1 * | 3/2002 | Naber et al. | 175/20 |
| 6,766,865 | B1 * | 7/2004 | Dagel et al. | 172/22 |
| 6,959,245 | B2 * | 10/2005 | Rooney et al. | 702/5 |
| 2005/0172733 | A1 * | 8/2005 | Drummond et al. | 73/864.41 |

* cited by examiner

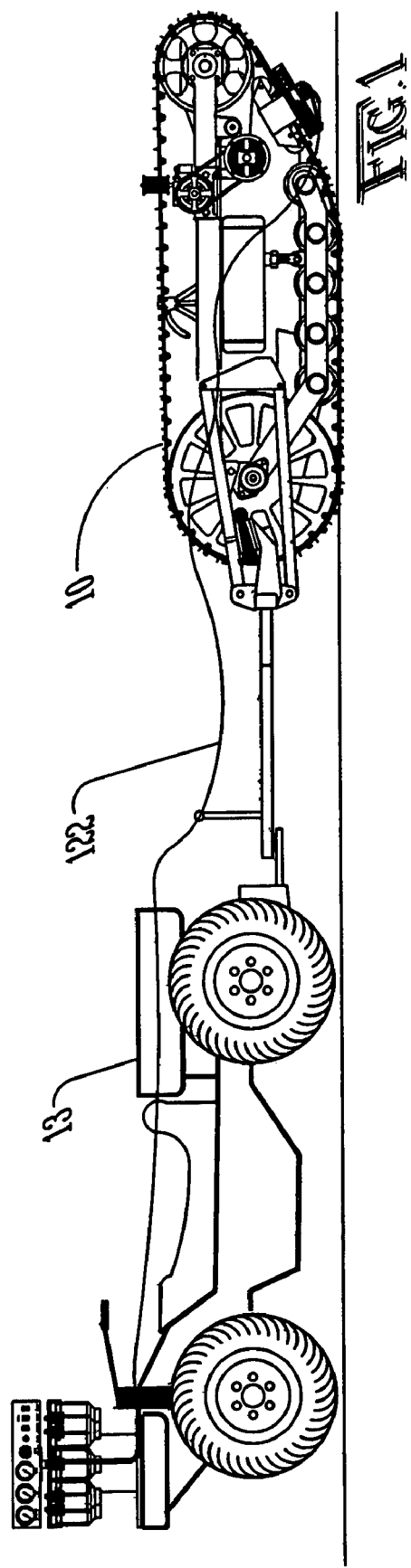

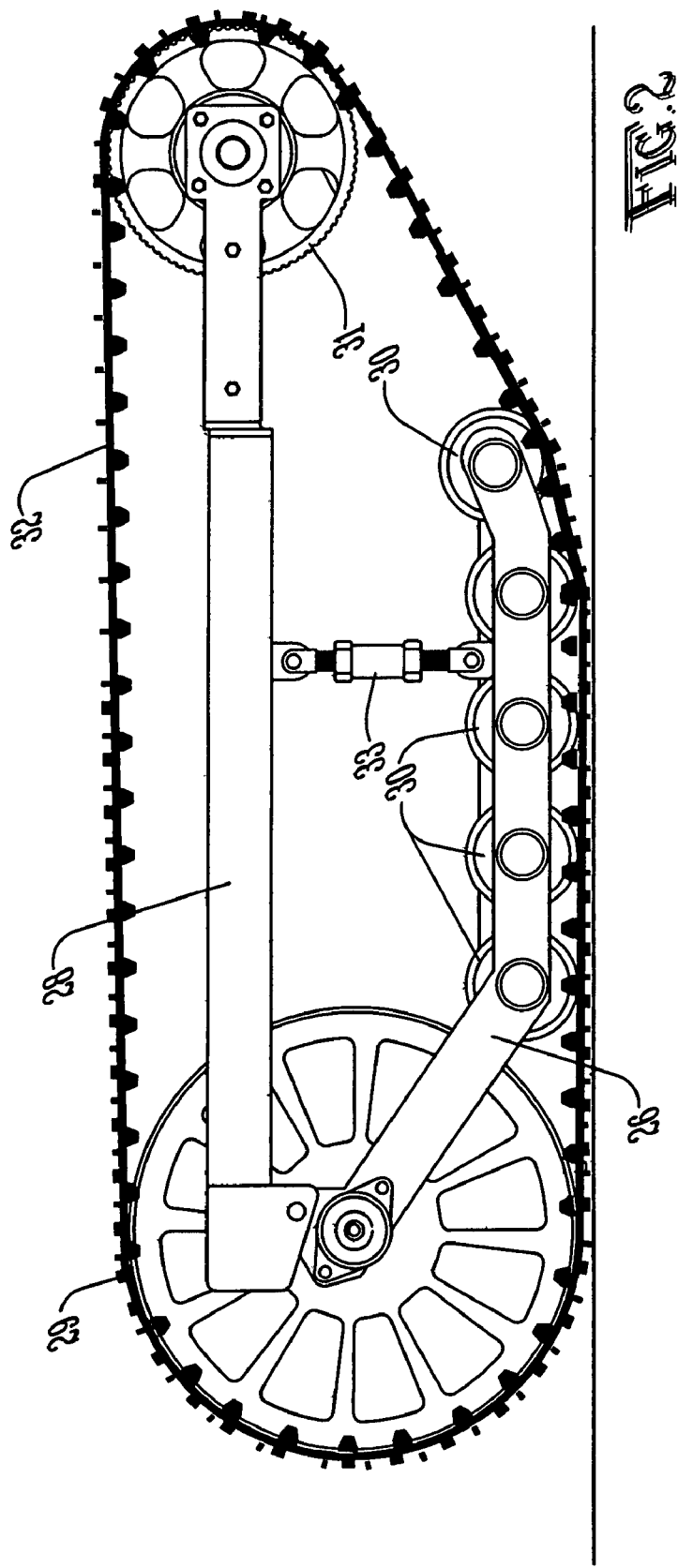

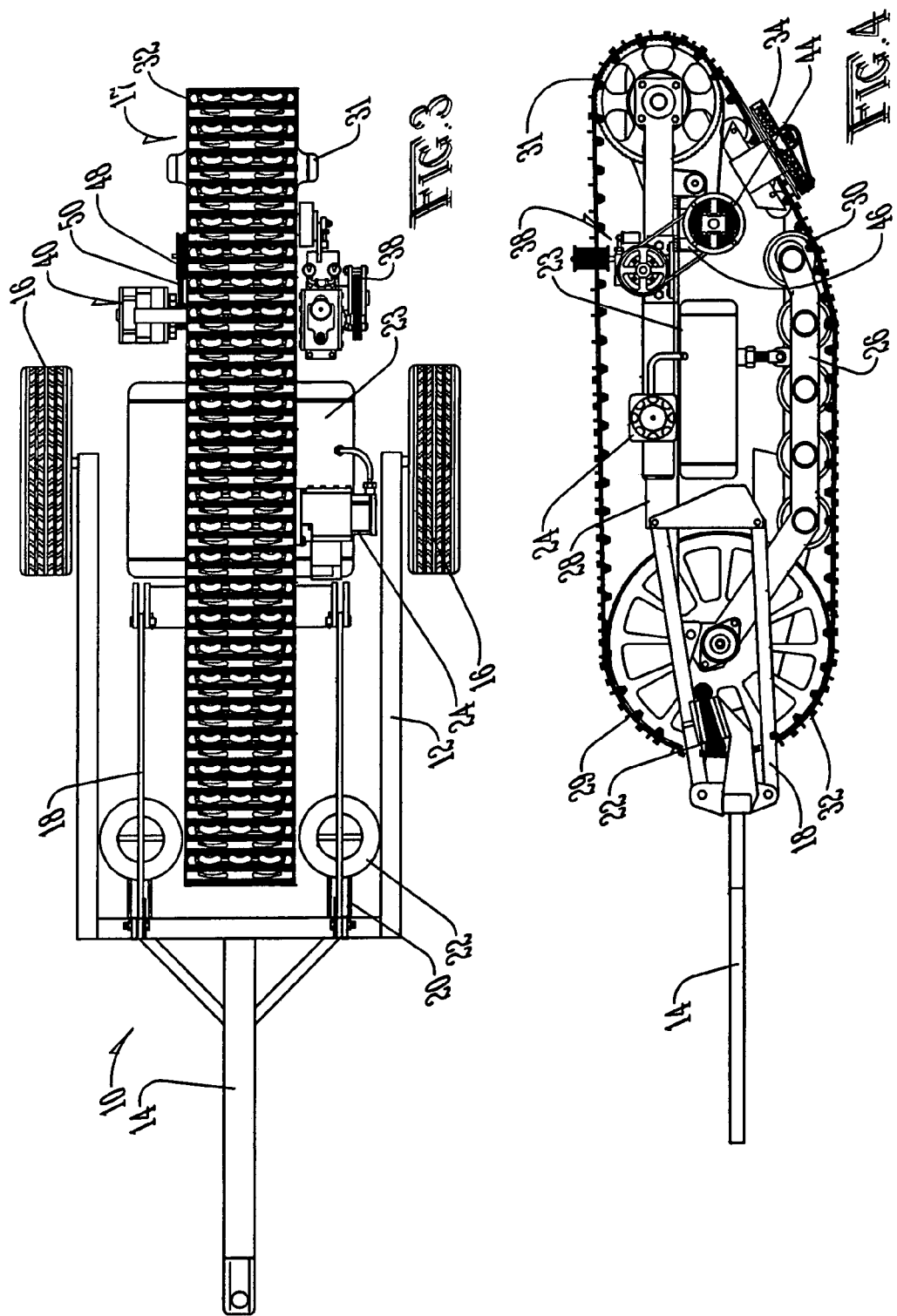

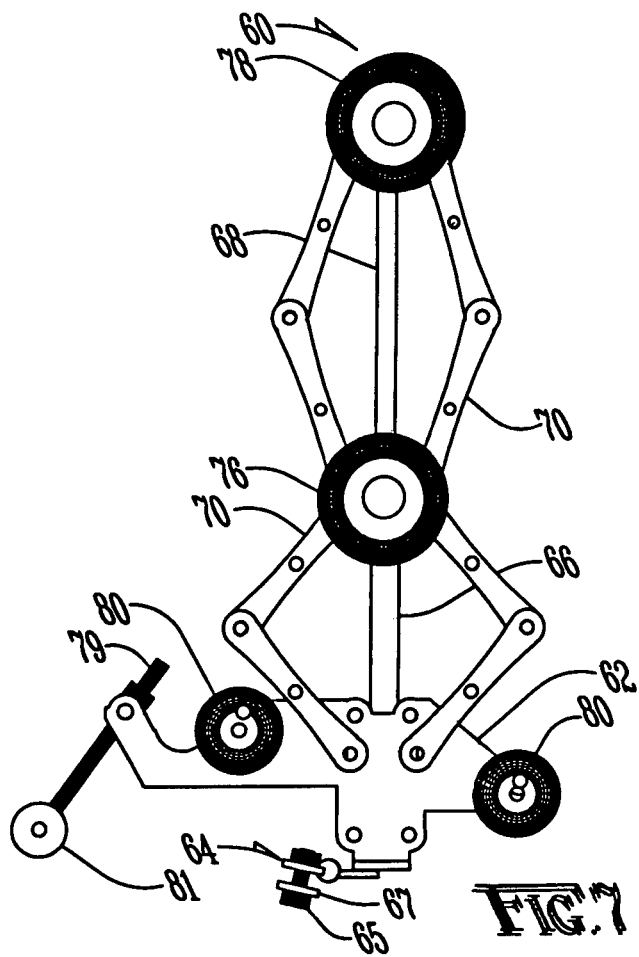
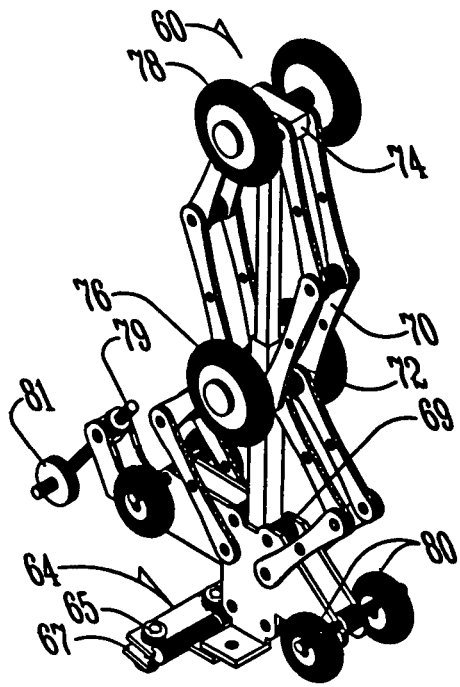

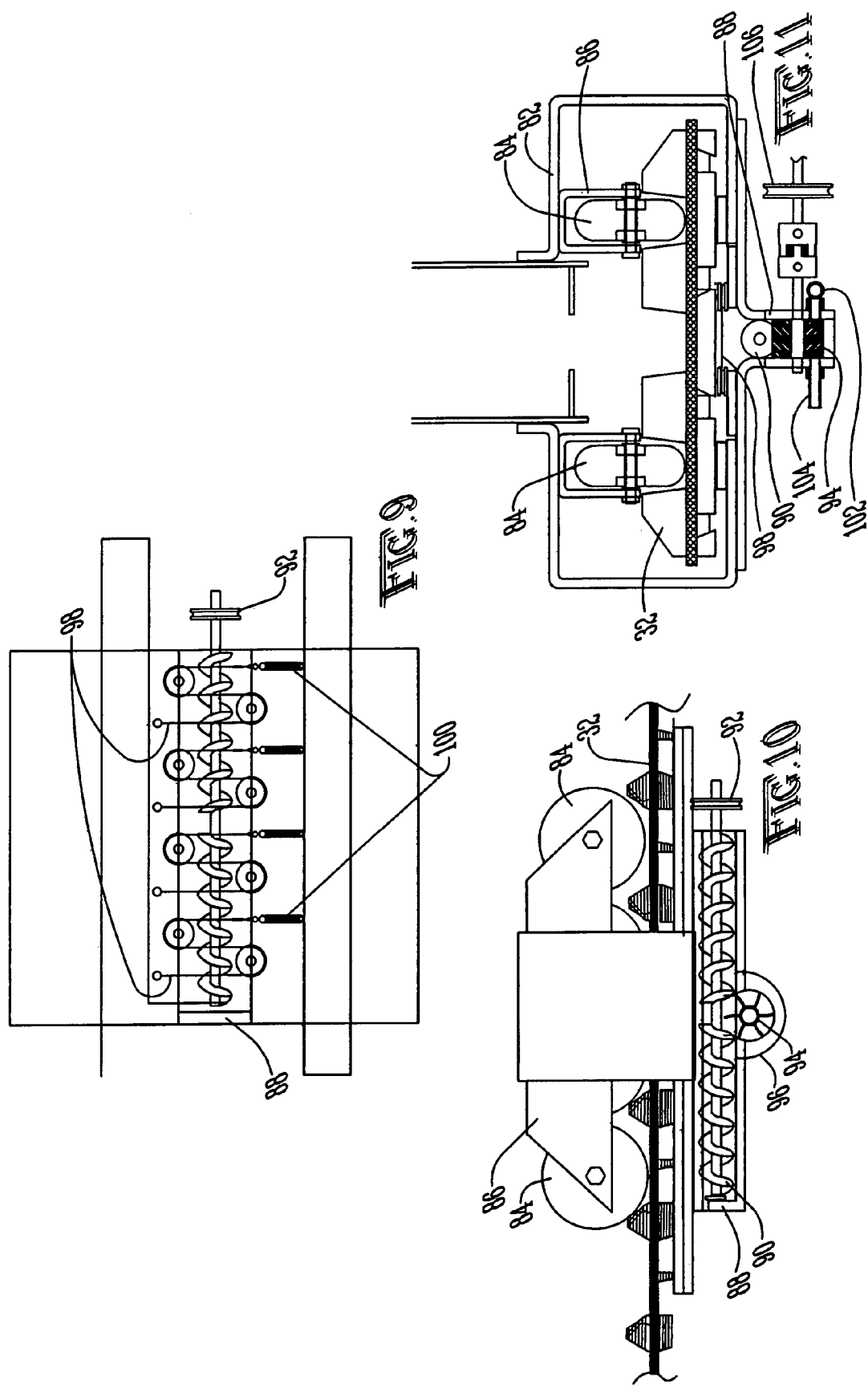

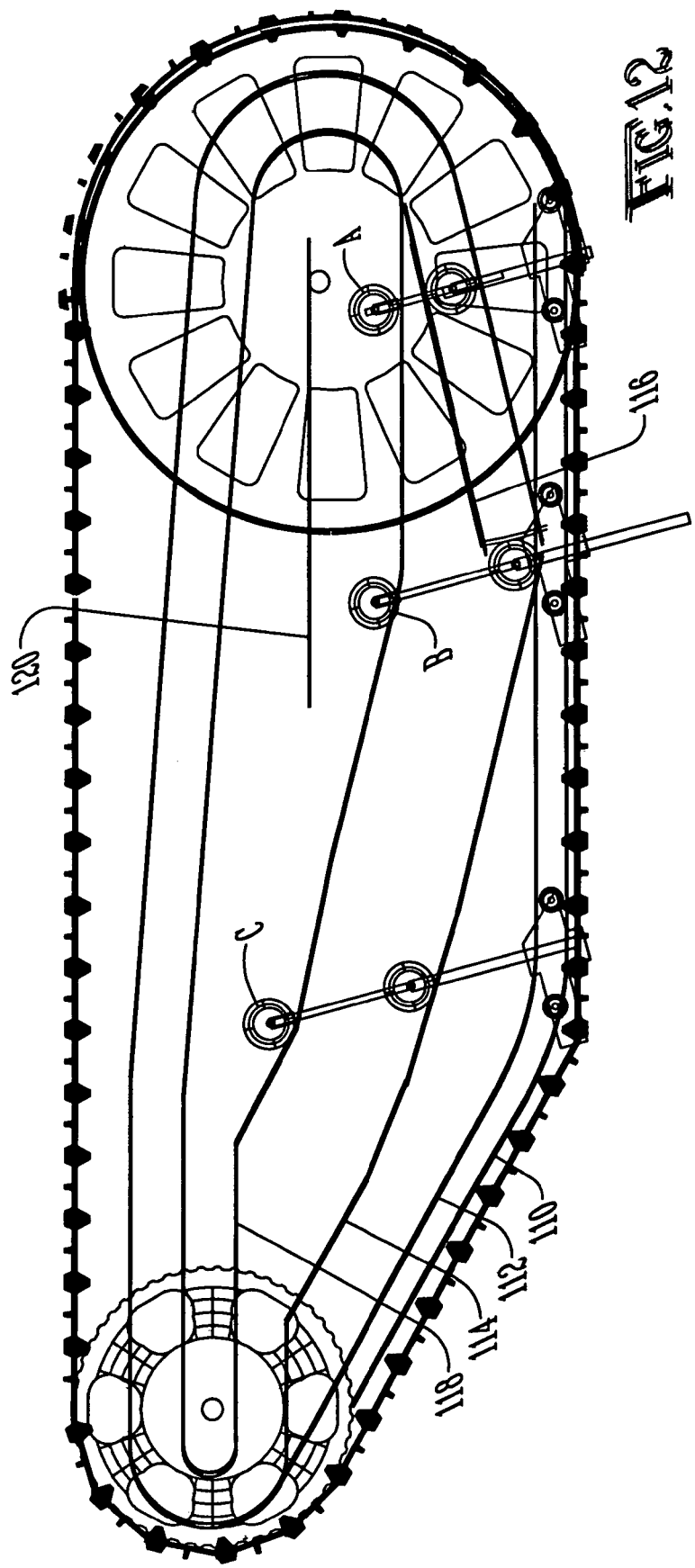

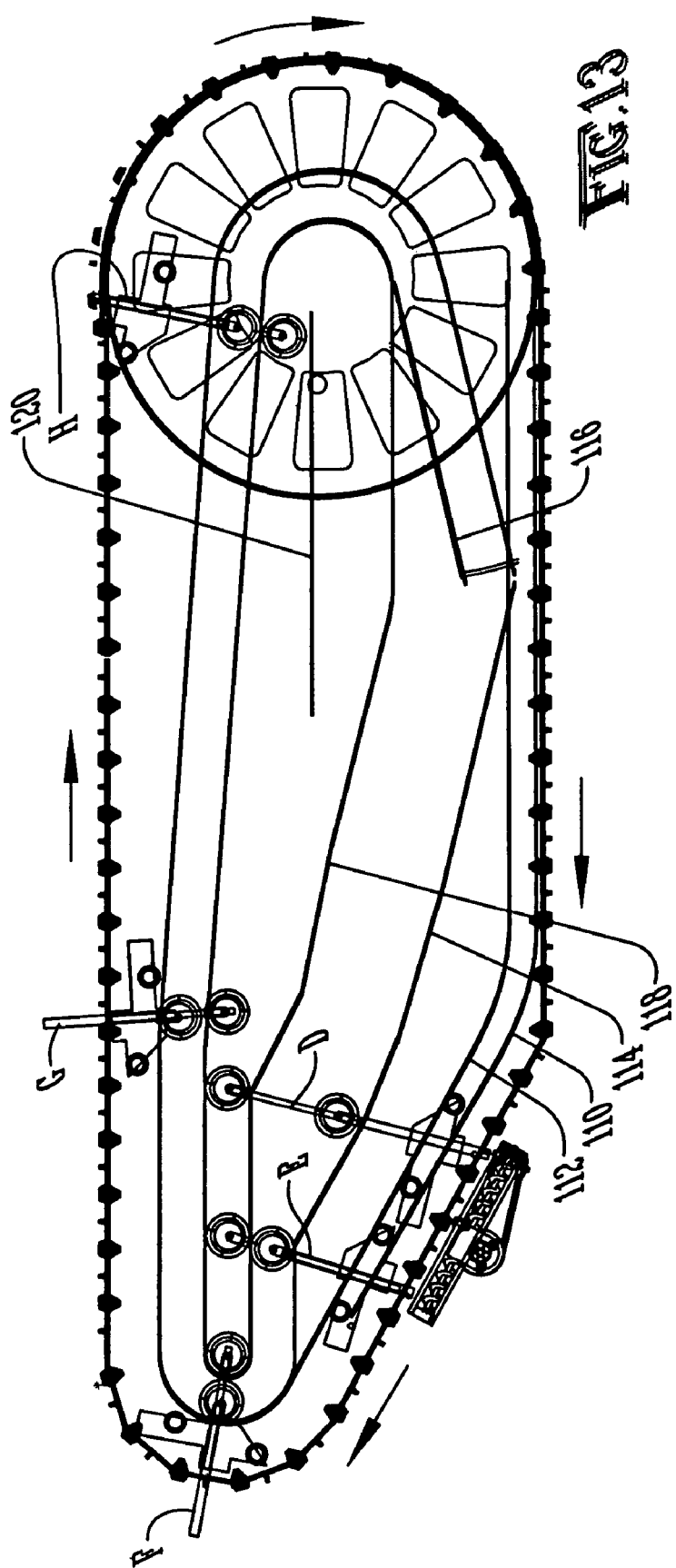

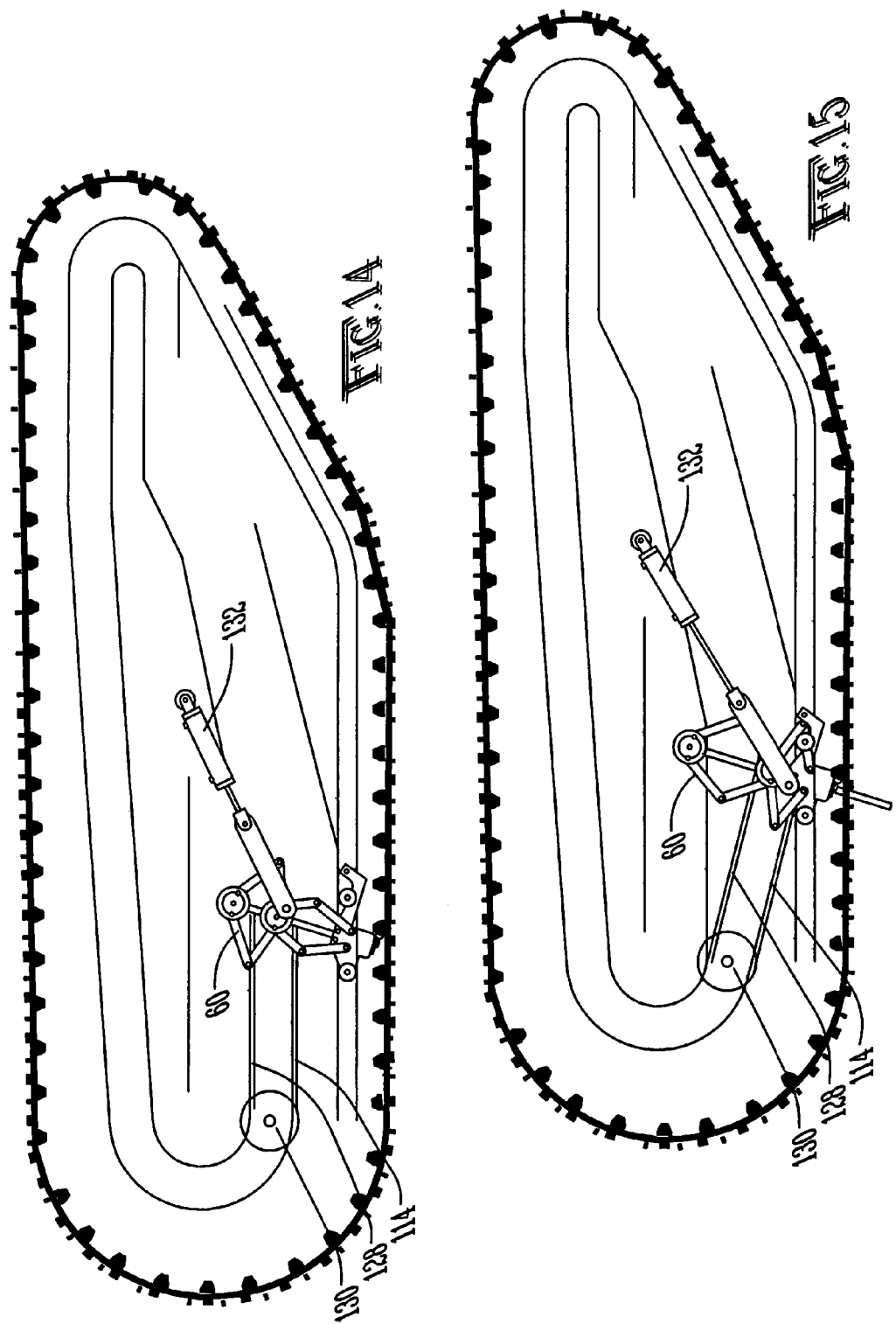

ly rely on the motion of a tractor or trailer wheel for activation cannot be used with a sampling vehicle that has no wheels, such as a boat or hovercraft. Even when such devices are used in conjunction with a wheeled vehicle, the sampling rate is tied to the distance traveled, and cannot be adjusted depending upon the growing conditions of a particular field. Further, systems that depend upon cams and linkages to perform the physical sampling process are subject to wear and failure of parts.

SOIL SAMPLER APPARATUS AND METHOD

This application is a continuation of and claims the benefit of U.S. utility patent application Ser. No. 10/548,907, filed on May 8, 2006 now U.S. Pat. No. 7,255,016, and entitled "Soil Sampler Apparatus and Method," which in turn claimed the benefit of international patent application no. PCT/US2004/007183, entitled "Soil Sampler Apparatus and Method," filed Mar. 9, 2004, which in turn claimed the benefit of U.S. provisional patent application No. 60/454,460, filed Mar. 13, 2003, entitled "Soil Sampler." The disclosure of each of such foregoing applications are incorporated herein by reference.

TECHNICAL FIELD

The present invention relates to soil sampling devices and methods, and in particular to soil sampling devices that periodically and automatically take soil samples over an area of interest, and related methods.

BACKGROUND ART

In order to optimize the production capacity of any agricultural land, the grower must provide in each plot of soil the amount of fertilizers and other nutrients and additives that will render each plot ideal for the crop that is to be sewn and harvested. The grower cannot know how much fertilizer or other additives should be placed at a plot of soil, however, without knowing the current level of nutrients and important minerals that are already present in each plot. The quantity of these various materials present will vary greatly depending upon the soil type, the history of crops grown, and additives that have been previously applied to the field. It is thus a common practice for growers to periodically remove soil samples from various regions on their agricultural lands, which are then analyzed to determine the level of various important nutrients and minerals that they contain.

Soil sampling has historically been a process performed by hand. Various hand tools have been developed to somewhat ease the burden of this task, but any manual operation to perform soil sampling is necessary tiresome and time-consuming because of the expanse of land that must be covered when soil sampling is performed as part of a large-scale commercial farming enterprise. Not only must a worker remove each sample, but the sample must then be transported back to a laboratory for analysis, and the samples must be transported in such a manner that samples from various plots are not mixed. Further, the samples must each be carefully labeled, and the worker must keep careful track of his or her location when each sample is removed. Because of the arduous nature of this task, growers typically take only one sample in a field of interest, or at most a few samples across a field or area of interest and then average the results. The farmer will then apply fertilizers and other nutrients to the soil as if the soil's level of nutrients were uniform across the field, which is in fact not generally the case. The result is a poor approximation of the optimal nutrient level for each plot of soil, since some plots will likely be under fertilized and others will be over fertilized. Under fertilized plots will produce poor yields, and over fertilized plots may both produce poorer than optimum yields and also result in a waste of fertilizers. The wasted fertilizer not only is an added expense for the grower, but also exacerbates environmental issues that may arise from the later run-off of the excessive fertilizer due to rain or wind.

With the wide availability of global positioning system (GPS) satellite receivers today, the use of GPS information in soil sampling is rapidly increasing. Currently it is believed that approximately 15% of total farm acreage in the United States (roughly 640 million acres) uses GPS information in conjunction with soil sampling efforts. It is expected that GPS usage will increase to encompass approximately 28% of total farm acreage by 2005. The use of GPS in conjunction with manual soil sampling, however, only provides modest improvements in accuracy and efficiency. Although the grower now has precise information about where each sample is taken, manual sampling procedures still require a worker to travel to each identified point in the field of interest, remove a sample by hand, and then label and transport that sample for analysis. Thus it would be highly desirable to develop a soil sampling system that would periodically sample the soil across a field, while automatically keeping track of where samples were removed using GPS information, and automatically separating the samples according to location for ease of analysis. Such a system would ideally allow the operator to simply direct the sampling mechanism around the field in a regular pattern, while the mechanism performs sampling in a manner that is automatic and effectively transparent to the operator.

The related art includes several attempts to develop soil sampling mechanisms that periodically sample soil over an area. U.S. Pat. No. 3,224,512 to Alexander teaches a soil sampler that is mounted on a trailer and powered by a hydraulic system. The device is intended to be pulled by a tractor around a field, and the motion of one of the vehicle wheels activates a piston and cam-drive arrangement in communication with the soil sampler's hydraulics. Since the sampling periodicity is driven by the motion of one of the wheels on the trailer, the device automatically samples soil at regular intervals, regardless of the speed of the tractor pulling the trailer. The device uses a sampling tube that is forced into the ground for sample collection. Since the device does not stop in order for samples to be taken, the sampling tube is designed to pivot upon entry into the ground. The sampling tube is returned to its original insertion position (angled toward the front of the trailer) by means of a spring.

U.S. Pat. No. 3,625,296 to Mabry et al. teaches another soil sampling device that is mounted on a trailer, and which is intended to periodically sample soil over which the trailer passes. A digger foot is used to collect the soil sample, the foot being mounted at the end of a lever that includes a cam follower at its opposite end. By means of the cam follower, a cam on one of the tractor's wheels forces the digger foot into the ground as the trailer travels, thereby scooping a soil sample. As the cam rolls forward, the digger foot is released and a spring biases the digger foot upward, where it strikes a bumper block and deposits the soil sample into a collection container. Like the Alexander device, the Mabry et al. device automatically samples soil at regular intervals, since its sampling periodicity is driven by the distance traveled by the cam-equipped tractor wheel.

U.S. Pat. No. 5,741,983 to Skotnikov et al. teaches a third trailer-mounted automatic soil sampling device. In this case, an odometer is used to monitor the distance of travel of the trailer, which drives the sampling period of the device. The device utilizes a shaft-drive and linkage arrangement to control the period of the sampling action based upon the rotation of one of the trailer's wheels. A complex linkage arrangement allows the sampling tube to be raised into a position to eject and deposit a sample during each sampling cycle. The device further includes a bagging mechanism, whereby each of the samples that are drawn from the ground may be automatically bagged and labeled for later laboratory analysis.

The automatic sampling mechanisms described above suffer from important disadvantages. Mechanisms that simple scoop a sample of material from the top of the ground are undesirable since such a sample may not be representative of the lower levels of the soil in the area that is sampled. The most relevant section of the soil is that section that will be in greatest contact with the roots of the crop to be planted, which in the case of almost all crops will be soil that lies at some distance below the surface. Further, in many applications the most desirable sample will be one that spans a section of the soil, from the surface to a pre-determined depth beneath the surface. A scooping mechanism will likely be unable to probe deeply enough to produce a sufficient sample to meet this need.

Although sampling mechanisms that insert a tube into the ground to collect a sample are superior to scoop mechanisms in many applications, the tube-type sampling mechanisms known in the art also suffer from disadvantages. It is desirable in an automatic sampling mechanism that the sample be taken without requiring the vehicle that is carrying the sampling mechanism to stop. This greatly simplifies the task of the operator of the vehicle, since sampling can be automatically performed as the operator follows a predetermined course over a field of interest, and also because it will save the operator a significant amount of time during the sampling process. The process of inserting and removing a tube from a moving vehicle, however, presents a number of difficulties. In one case these difficulties have been addressed by the use of a tube that pivots, thereby allowing the tube to be inserted into the ground at a forward-sloped angle, while it pivots rearwardly until the tube is removed. Depending upon the hardness of the soil, however, this may create a great deal of stress upon the tube. The pivoting action causes the tube to push backward against soil that is rearward of the tube at its distal end, and push forward against soil that is forward of the tube at its proximal end. While this may be a workable solution in very loose, highly compressible soil, this will likely lead to bending, excessive wear, or other damage to the tube in more firmly packed soil, or soil that may contain rocks or other hard obstacles.

Another solution to the problem of vehicle motion while the tube is inserted in the ground is a complex linkage arrangement that allows the structure immediately supporting the sampling tube to "follow" the tube during the portion of the sampling cycle when the tube is inserted into the ground. While this arrangement may avoid the problems presented by tube rotation, the structure and linkages necessary for this functionality are complex, and would likely be expensive to manufacture and difficult to maintain.

Another disadvantage of the systems described above is that they do not take advantage of the efficiencies that may be achieved with the use of GPS information during sampling. Mapping of a field of interest, and selection of areas within the field for individual analysis, is greatly simplified using GPS information, and furthers the goal of making the process as transparent and automatic for the operator as possible.

What is desired is an automatic soil sampling mechanism that facilitates the sampling of soil across an area of interest by simply tracing the mechanism over the area, while also being inexpensive to manufacture and simple to maintain, and taking advantage of GPS information. The limitations of the prior art are overcome by the present invention as described below.

DISCLOSURE OF INVENTION

The present invention is directed to an automatic soil sampling apparatus that comprises a sampling assembly that revolves around a continuous track while the apparatus is in motion. The mechanism may be mounted on a trailer or other like vehicle. The drive mechanism for the sampling assembly is powered by the movement of the vehicle as the track maintains contact with the ground. The sampling assembly revolves with the continuous track of the drive mechanism, allowing it to retrieve soil samples as it passes over the ground during each revolution. Since the drive mechanism is powered by the vehicle's motion with respect to the ground, the sampling assembly will in effect be stationary with respect to the ground as it is passing along that portion of the continuous track's path that is in contact with the ground. Thus the sampling tube of the sampling assembly may be inserted into the ground and removed while passing along the bottom portion of the drive without the need for a pivoting action or complex linkages in order to hold the tube in a particular position while the sample is collected. A rail or guide arrangement, against which the sampling assembly rides, may be used to extend and retract the sampling tube, while also extending and retracting an ejector bar within the sampling tube in order to remove the sample from the sampling tube.

Soil cores ejected from the sampling tube fall into a collection tray, which in certain embodiments may include a wire grid to break the sample into smaller portions, and an auger system to direct soil into a delivery tube beneath the tray. A pneumatic delivery system may be used in certain embodiments to move collected samples from the collection tray to sample storage containers, which may be located adjacent the operator of a vehicle pulling the sampling mechanism for ease of access. A rotating tray with multiple storage containers may be employed in certain embodiments in order to collect samples. A computer-based GPS mapping system may be used in conjunction with the present invention in order to coordinate the mapping of a field of interest and collection of samples at appropriate locations.

It is therefore an object of the present invention to provide for a soil sampling mechanism that may automatically collect soil samples over an area of interest.

It is a further object of the present invention to provide for a soil sampling mechanism that provides sampling tubes that are stationary with respect to the ground during a portion of the sampling cycle so that the tube may be easily inserted and retracted from the ground in order to collect samples.

It is also an object of the present invention to provide for a soil sampling mechanism that is inexpensive to produce and easy to maintain.

It is also an object of the present invention to provide for a soil sampling mechanism that allows for the pneumatic movement of collected samples from a collection tray to a location more convenient to an operator.

It is also an object of the present invention to provide for a soil sampling mechanism that allows the automatic collection of a number of soil samples in a plurality of containers on a rotating tray for ease of analysis.

It is also an object of the present invention to provide for a soil sampling mechanism that allows for the use of a computer-based mapping system in order to map an area of interest and collect samples from the appropriate portions of the area of interest.

These and other features, objects and advantages of the present invention will become better understood from a consideration of the following detailed description of the preferred embodiments and appended claims in conjunction with the drawings as described following:

BRIEF DESCRIPTION OF DRAWINGS

FIG. 1 is a side elevational view of a preferred embodiment of the present invention including a tow vehicle.

FIG. 2 is a side elevational view of the drive components of a preferred embodiment of the present invention.

FIG. 3 is a top plan view of a preferred embodiment of the present invention.

FIG. 4 is a side elevational view of a preferred embodiment of the present invention, in partial cut-away along line Z-Z of FIG. 3.

FIG. 7 is a side elevational view of a sampler assembly from a preferred embodiment of the present invention.

FIG. 8 is a perspective view of a sampler assembly from a preferred embodiment of the present invention.

FIG. 9 is a top plan view of a soil collection hopper assembly according to a preferred embodiment of the present invention.

FIG. 10 is a side elevational view of a soil collection hopper assembly according to a preferred embodiment of the present invention, in partial cut-away along line A-A of FIG. 9.

FIG. 11 is an end elevational view of a soil collection hopper assembly according to a preferred embodiment of the present invention, in partial cut-away along line B-B of FIG. 9.

FIG. 12 is a progressive view of the motion of a sampling probe of a preferred embodiment of the present invention during the soil probe cycle.

FIG. 13 is a progressive view of the motion of a sampling probe of a preferred embodiment of the present invention during the soil ejection and return cycle.

FIG. 14 is a progressive view of the motion of a sampling probe in the bypass position according to a preferred embodiment of the present invention.

FIG. 15 is a progressive view of the motion of a sampling probe in the probe position according to a preferred embodiment of the present invention.

BEST MODE FOR CARRYING OUT THE INVENTION

Figure 5:
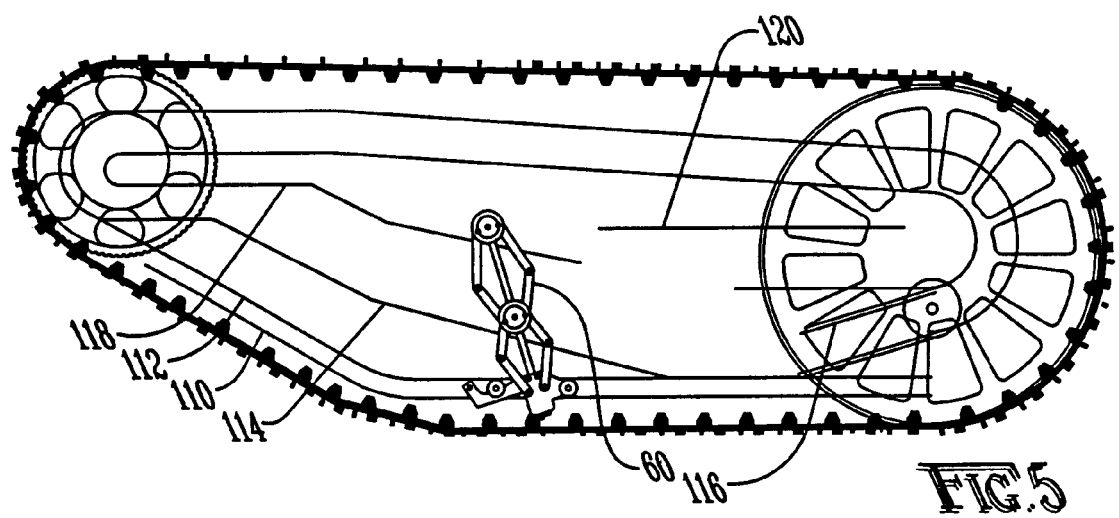
FIG. 5 is a perspective view of the sampler assembly track components from a preferred embodiment of the present invention.

With reference to FIGS. 1-4, the preferred embodiment of the present invention may be described. The support structure of the preferred embodiment is provided by a trailer 10, which may include a U-shaped frame 12, a tongue 14, and support wheels 16. These components provide support for drive mechanism 17. In the preferred embodiment, wheels 16 are standard automobile wheels with rubber tires, but various other forms of wheels 16 may be employed such that trailer 10 may be easily pulled across cultivated soil as well as ferried to and from the field along paved or unpaved roads. Tongue 14 may be hitched to an all-terrain vehicle (ATV), tractor, or other powered vehicle 13 for the movement of the preferred embodiment in the field or other region where sampling is desired. Although the preferred embodiment of the invention is not powered, and thus relies on vehicle 13 for movement, alternative embodiments might include any form of drive mechanism 17 that is integrated with the other components of the invention, such that no separate vehicle 13 is required.

Attached to U-shaped frame 12 is drive mechanism support frame 18. Drive mechanism support frame 18 preferably comprises two longitudinally arranged bars on either side of the drive mechanism of the device, but any alternative arrangement that provides support from U-shaped frame 12 to the drive mechanism may be used. Support frame 18 is attached to U-shaped frame 12 at attachment blocks 20 such that the drive mechanism 17 may be raised or lowered with respect to U-shaped frame 12. The raising of drive mechanism 17 is accomplished by the inflation of air stroke cylinders 22. Air stroke cylinders 22 ride against a structural component of U-shaped frame 12 and beneath the upper longitudinal arms of support frame 18. Filling air stroke cylinders 22 with air causes the upper longitudinal arms of support frame 18 to rise, thereby raising drive mechanism 17 off of the ground. In this manner, the device may be transported without the operation of the sampling mechanism, such as when the device is being moved to or from a field for sampling, ferrying between fields, or when turning a corner at the end of a sampling row. Air to fill air stroke cylinders 22 is maintained in air tanks 23, which are filled by air compressor 24 through an air line (not shown for clarity). In the preferred embodiment, air compressor 24 is powered by a 12-volt automotive battery (not shown), which may be mounted at any convenient location on trailer 10, such as above tongue 14. The charge in the battery is maintained through the operation of alternator 40. In alternative embodiments of the invention, air stroke cylinders 22 may be replaced by other means for raising and lowering drive mechanism 17, such as lineal actuators or hydraulic cylinders.

Support frame 18 connects to drive mechanism 17 through lower frame members 26 and upper frame members 28. The two front idler wheels 29 are disposed between the forward ends of lower frame members 26 and upper frame members 28. Each of front idler wheels 29 ride on a flange-mount roller bearing attached at the forward ends of each of lower frame members 26, and are connected by a common axle (not shown). Also attached at each of lower frame members 26 are ground wheels 30. Like front idler wheels 29, ground wheels 30 are mounted on roller bearings. In the preferred embodiment, a total of five ground wheels 30 are employed on each side of drive mechanism 17. Sandwiched between the rear ends of upper frame members 28 are rear idler wheels 31. Like front idler wheels 29, rear idler wheels 31 rides on an bearings with no central axle; in the case of rear idler wheels 31, the bearings are mounted at the rearward ends of upper frame members 28. It may be noted that in alternative embodiments of the invention, various numbers of idler wheels and ground wheels may be employed. The key considerations are that sufficient support for drive mechanism 17 must be provided, and sufficient space must be maintained in the interior of drive mechanism 17 for the cycling of the sampling equipment as described hereafter. By way of example, one possible alternative embodiment would involve four wheels set in a roughly rectangular arrangement, with the omission of the ground wheels. Many other configurations are possible within the scope of the present invention.

Rotating around front idler wheels 29, ground wheels 30, and rear idler wheels 31 is track 32. Track 32 is preferably constructed of rubber, and includes tread or cleats on the exterior in order to engage the ground without significant slippage during operation. To the interior of track 32 are alignment lugs that are positioned to either side of each of front idler wheels 29 and rear idler wheels 31 during rotation, such that track 32 is engaged with front idler wheels 29 and rear idler wheels 31, and the revolution of track 32 will cause these wheels to turn and prevent slippage of track 32 from front idler wheels 29 and rear idler wheels 31. As will be apparent from this description, the lowering of drive mechanism 17 by the release of pressurized air from air stroke cylinders 22 will cause track 32 to make firm contact with the ground. The weight of drive mechanism 17 will cause the traction elements of track 32 to engage the ground when trailer 10 is being pulled, and thus cause track 32 to rotate around front idler wheels 29, ground wheels 30, and rear idler wheels 31. The speed of track 32 during rotation will precisely match the ground speed of trailer 10, provided no significant slippage between the ground and track 32 occurs. The rotation of track 32 about the idler wheels and ground wheels of the preferred embodiment should be sufficiently free that no slippage occurs between track 32 and front idler wheels 29 and rear idler wheels 31. If drive mechanism 17 is raised by the inflation of air stroke cylinders 22, then track 32 will cease to revolve since it is no longer in contact with the ground.

As shown in FIG. 2, turnbuckle adjustment 33 provides adjustable pressure to hold apart lower frame members 26 and upper frame members 28, thereby maintaining the proper tension on track 32. Proper tension is necessary to ensure that track 32 properly tracks during rotation with respect to front idler wheels 29 and rear idler wheels 31.

It may be noted that as track 32 passes front idler wheels 29 and passes under ground wheels 30, any given location on track 32 that is in contact with the ground maintains contact with the same section of ground until it again rises into the air toward the last ground wheel 30. This is an inherent property of any drive arrangement employing a track revolving around a plurality of sprockets or wheels. The invention takes advantage of this characteristic since the insertion and retraction of a sampler that follows track 32 may be performed without movement of the sampler with respect to the ground, as will be described hereafter.

While in the preferred embodiment the ground engagement of the invention is provided by rubber track 32, many other engagement means may be employed in alternative embodiments. Metal tracks could be employed, which are commercially available. Another embodiment may feature a pair of roller chains that rotate about sprocket pairs, with cross pieces fitted between the roller chains forming in effect a track-type arrangement. Channel iron in a "C" shape may be ideal for this embodiment since the rides forming the arms of the "C" shape may be faced outwardly in order to provide traction for drive mechanism 17. In another alternative embodiment, track 32 may be replaced simply with wheels that contact the ground and transfer their rotational energy, through mechanical linkages or otherwise, to a set of sprockets or wheels that drive the revolution of the sampling mechanism. In yet another alternative embodiment, a powered drive system may be employed, such that the sampling mechanism rotates under power from a motor, engine, or the like, and no direct contact between the ground and any drive mechanism is in fact required.

Also mounted at one of upper frame members 28 is rotary vane compressor 38. Compressors of the rotary vane type are well known in the art and widely available commercially. Compressor 38 is connected to soil ejection hopper assembly 34 by an air line (not shown for clarity), the operation of which is described hereafter. Compressor 38 is powered by one of rear idler wheels 31 through an idler belt (not shown for clarity). Two idler belts are employed in the preferred embodiment, one corresponding to each rear idler wheel 31, with each of the idler belts sandwiched between rear idler wheels 31 and track 32. In the case of the idler belt on the same side of drive mechanism 17 as compressor 38, the idler belt engages gearbox 44, which affects a step-up of rotational speed from rear idler wheel 31. In the preferred embodiment, a gearbox 44 with a step-up ratio of about 3.5 to 1 is employed. This provides sufficient rotational velocity to drive compressor 38. The gearbox then drives compressor 38 by means of compressor belt 46. On the opposite side of drive mechanism 17, the other idler belt revolves around the opposite rear idler wheel 31 and engages an inner sheave (not visible in FIG. 3) on jackshaft 48. Because of the different sheave sizes on jackshaft 48, a step-up in rotational speed is achieved; a step-up ratio of about 3 to 1 is employed in the preferred embodiment. Alternator 40 is thus driven from jackshaft 48 by alternator belt 50. As a result of this arrangement, whenever drive mechanism 17 is lowered and track 32 is turning, compressed air will be reaching soil ejection hopper assembly 34 from rotary vane compressor 38, and alternator 50 will be charging the battery of the device.

Figure 6:
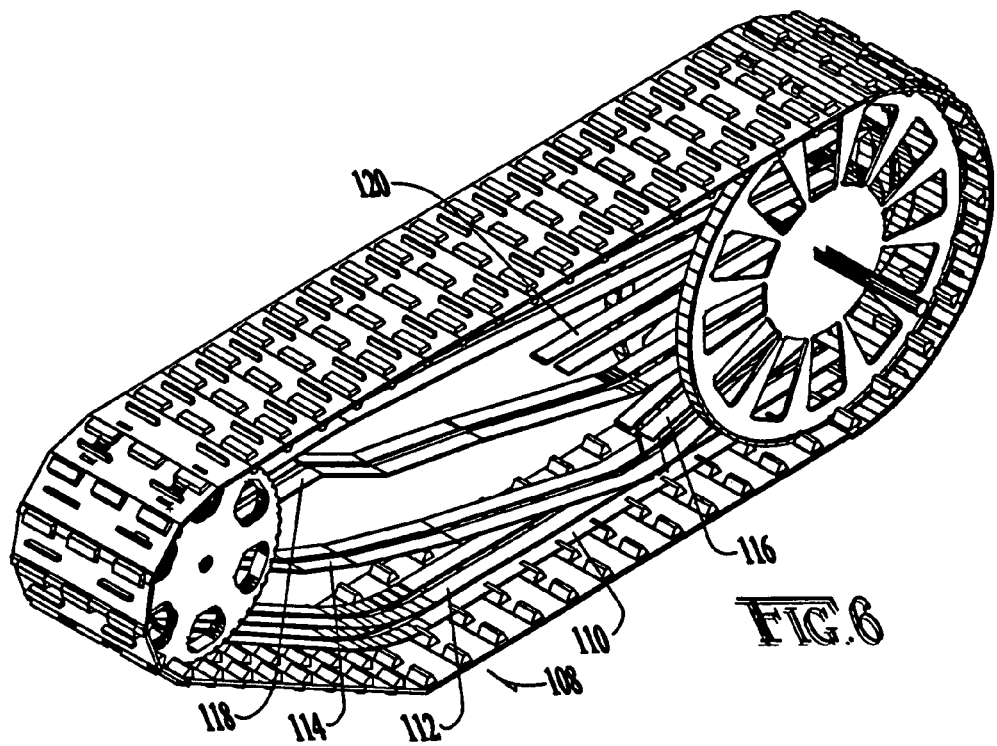
FIG. 6 is a side elevational view of the sampler assembly track components from a preferred embodiment of the present invention.
Figure 16:
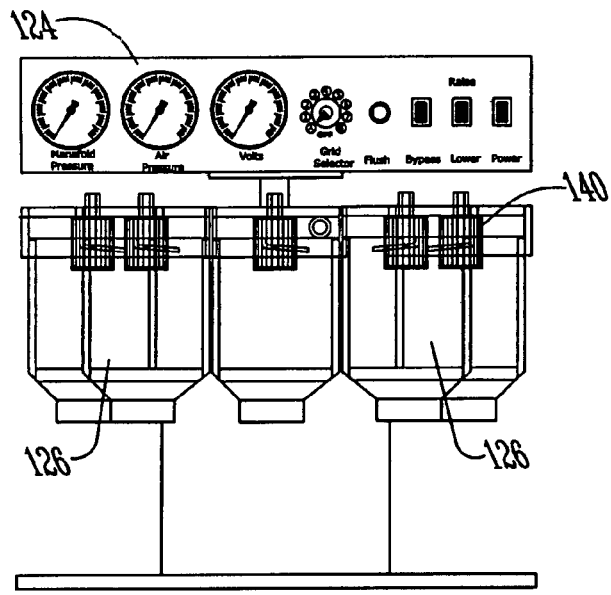
FIG. 16 is a plan elevational view, in partial cut-away, of the sample collection system according to a preferred embodiment of the present invention.
Figure 17:
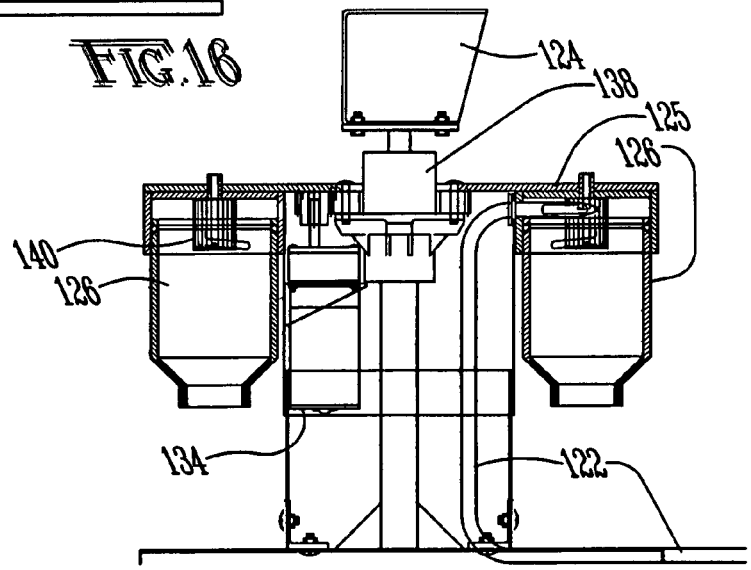
FIG. 17 is a plan elevational view of the sample collection system according to a preferred embodiment of the present invention, in partial cut-away along line A-A of FIG. 16.
Figure 18:
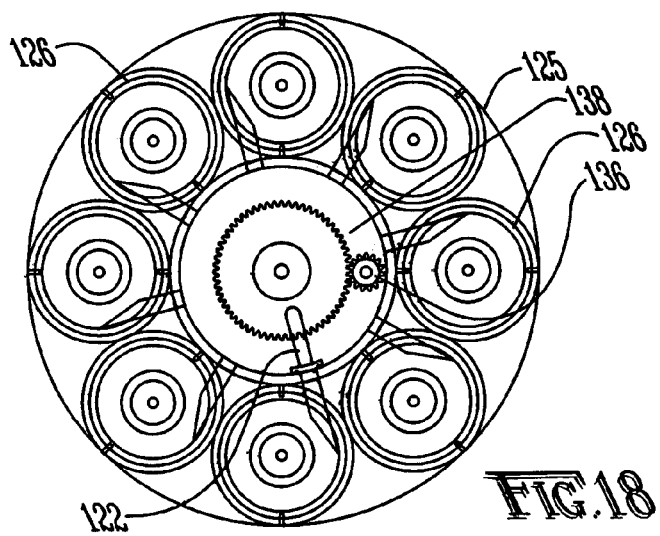
FIG. 18 is a plan elevational view of the sample collection system according to a preferred embodiment of the present invention, in partial cut-away along line B-B of FIG. 16.

Referring now in particular to FIGS. 5-8, the structure of a preferred embodiment of a sampler assembly 60 according to the invention may be described. Sampler base 62 is preferably formed of two steel plates that are spaced slightly apart. Sampler base 62 is attached to track 32 at base hinge 64. Base hinge 64 allows sampler assembly 60 to pivot with respect to track 32 during operation. Base hinge 64 is attached to track 32 by means of base bolts 65, which pass through track 32 engaging base hinge 64 on one side and base hinge plate 67 on the other. Track 32 is thus sandwiched between base hinge 64 and base hinge plate 67. As a result of this attachment, sampler assembly 60 rotates with track 32 as track 32 turns around front idler wheels 29 and rear idler wheels 31, with sampler assembly 60 remaining between each pair of wheels during this process, and further allowing sampler assembly 60 to pivot with respect to track 32 in order to negotiate all necessary turns during revolution.

Probe 66 is positioned perpendicularly to sampler base 62, such that it is extendible between the plates forming sampler base 62. Probe 66 rides on rollers 69; in the preferred embodiment there are four rollers 69 sandwiched between the sides of sampler base 62 (one roller 69 is visible in FIG. 8). Rollers 69 ride on pins that connect between the sides of sampler base 62. Rollers 69 function to guide probe 66 as it passes between the sides of sampler base 62. Probe 66 is thus prevented from rocking backward or forward with respect to sampler base 62 by four rollers 69.

The point at which sampler assembly 60 is attached to track 32 features an aperture that is sized to receive probe 66. As a result, probe 66 is extendible through track 32 in order to probe into the soil in a manner that will be described in greater detail hereafter. In the preferred embodiment, probe 66 is constructed from square stainless steel tubing that is about 1.27 cm in width. Stainless steel is preferred in order to reduce the likelihood of corrosion on probe 66, which may affect the performance of the device. The tubing is preferably annealed for additional strength. Many other configurations may be used in alternative embodiments, including round steel tubing, but square tubing was chosen in the preferred embodiment for ease of manufacture and maintenance.

Slideably fitted within probe 66 is ejector 68. Ejector 68 is moveable from a position where it retracts outwardly from the end of probe 66 such that it is almost entirely outside of probe 66, to a point where it extends through the full length of probe 66. Ejector 68 is preferably formed of square stainless steel rod that is about 0.79 cm in width. The rod is preferably annealed for additional strength. Many other configurations are possible, with ejector 68 preferably fitting snugly within probe 66 but not so tightly that its freedom of movement within probe 66 is significantly limited by friction. Ejector 68 may, in the preferred embodiment, include a wiper (not shown) attached to the distal end of ejector 68, which extends into and through probe 66. In a preferred embodiment, the wiper may be formed of ultrahigh molecular weight (UHMW) polyethylene, or a similar soft and durable material. The purpose of the wiper is to ensure that all sample material within probe 66 is ejected when ejector 68 passes through probe 66, without allowing soil or other debris to be trapped between the inner wall of ejector 68 and probe 66.

Scissor frame assembly 70 supports probe 66 and ejector 68 in position with respect to sampler base 62. In the preferred embodiment, scissor frame assembly 70 may be constructed from individual annealed stainless steel links that are similar to steel roller chain but with increased pitch. The links are pinned, bolted, or otherwise attached, preferably using roller chain pins, bushings, and rollers, in such a manner as to form a collapsing double-scissor arrangement as shown in FIGS. 7 and 8. Scissor frame assembly 70 is attached to sampler base 62 by pins or other means. Scissor frame assembly 70 is attached at or near the proximal end of probe 66 at lower link point 72, and is attached at or near the proximal end of ejector 68 at upper link point 74. These connections are preferably bolted or otherwise attached in a manner to allow rotation, since the individual link components of scissor frame assembly 70 must pivot with respect to probe 66, ejector 68, and base 62 as scissor frame assembly 70 compresses and expands. In the preferred embodiment, scissor frame assembly 70 may be biased by internal springs (not shown) to assume a collapsed shape, whereby probe 66 extends through sampler base 62 and ejector 68 extends fully into probe 66.

Attached at lower link point 72 of scissor frame assembly 70 are a pair of probe guide wheels 76. Probe guide wheels 76 are attached to either side of probe 66 and hingeably linked to scissor frame assembly 70 at lower link point 72. Probe guide wheels 76 thus travel up and down with probe 66 as the lower portion of scissor frame assembly 70 compresses and expands. Probe guide wheels 76 preferably travel on ball bearings, and may rotate freely. Likewise, attached at upper link point 74 of scissor frame assembly 70 are a pair of ejector guide wheels 78. Ejector guide wheels 78 are attached to either side of ejector 68 and hingeably linked to scissor frame assembly 70 at upper link point 74. Ejector guide wheels 78 thus travel up and down with ejector 68 as the upper portion of scissor frame assembly 70 compresses and expands. Like probe guide wheels 76, ejector guide wheels 78 preferably travel on ball bearings, and may rotate freely. Probe guide wheels 76 and ejector guide wheels 78 function as followers to manipulate sampler assembly 60 in a manner that will be described hereafter. It will be seen, however, that as a result of this arrangement of sampler assembly 60, the application of upward pressure on probe guide wheels 76 will cause probe 66 to retract against the bias of the springs of the lower section of scissor frame assembly 70. Likewise, it will be seen that the application of upward pressure on ejector guide wheels 78 will cause ejector 68 to retract from within probe 66 against the bias of the springs of the upper section of scissor frame assembly 70. Alternative embodiments may include various other types of followers, including sliding followers rather than the rotating followers implemented in the form of probe guide wheels 76 and ejector guide wheels 78.

In addition to probe guide wheels 76 and ejector guide wheels 78, sampler assembly 60 preferably includes two additional pairs of wheels in the form of base guide wheels 80. Like probe guide wheels 76 and ejector guide wheels 78, base guide wheels 80 are mounted on ball bearings or otherwise such that they may freely rotate. The purpose of base guide wheels 80 is to hold sampler assembly 60 in position as it rotates with track 32 in a manner as will be described hereafter.

Also attached to sampler base 62 for purposes of holding sampler assembly 60 in position as it rotates is strut 79. Strut 79 is preferably formed from steel rod, and features a threaded proximal end to receive a nut. Strut 79 is connected between the sides of sampler base 62 through a pivoting block (not shown) that is pinned between the sides of sampler base 62. Strut 79 is inserted through an aperture in this block such that strut 79 may freely slide longitudinally within this block. The nut on the proximal, threaded end of strut 79 stops the travel of strut 79 within this block at the proximal end. Strut 79 is pinned to track 32 at its distal end by the insertion of a pin (not shown) through track 32 and connector 81. In alternative embodiments, strut 79 may be fastened to track 32 by any other secure means. As a result of this arrangement, sampler assembly 60 may rock forward and backward with a limited degree of freedom, thereby allowing sampler assembly 60 sufficient freedom of movement that sampler assembly 60 may negotiate the turns at the idler wheels of drive mechanism 17 without damage to sampler assembly 60.

Referring now to FIGS. 9-11, the construction of hopper assembly 34 according to a preferred embodiment of the present invention may be described. Hopper bracket 82 provides support for a pair of hopper wheel frames 86. Four hopper wheels 84 are mounted to each of the two hopper wheel frames 86 such that hopper wheels 84 ride against track 32. Hopper wheels 84 are mounted on ball bearings or otherwise in order to allow them to rotate freely as track 32 passes underneath.

Also mounted to hopper bracket 82 but beneath track 32 is hopper 88. Hopper 88 is preferably formed as an elongated, U-shaped trough, aligned longitudinally with and at the center of track 32, with an open top to receive soil. It will be seen that as probe 66 revolves with track 32, it will pass over the full length of hopper 88. Soil from probe 66 may thus be deposited in hopper 88 through the aperture in track 32 beneath probe 66 as probe 66 passes over hopper 88 in a manner as will be described hereafter.

Referring specifically now to FIG. 9, soil slicing wires 98 are disposed above the open top of hopper 88, and held in appropriate tension by tensioning springs 100. As soil is deposited into hopper 88 as hopper 88 is passed over by probe 66, the soil will be tightly packed and might cause hopper 88 to clog. The purpose of slicing wires 98 is to break up the soil into smaller chunks before reaching the bottom of hopper 88. While soil slicing wires 98 and tensioning springs 100 form a part of the preferred embodiment of the invention, these elements may be omitted from alternative embodiments of the invention if soil conditions do not warrant their use.

Referring again to each of FIGS. 9-11, disposed within and along the length of hopper 88 is auger 90. Auger 90 is sized to fit snugly within the U-shaped trough formed by hopper 88. The blade portion of auger 90 is formed in a clockwise rotational direction over one half of hopper 88, and is formed in a counter-clockwise rotational direction over the other half of hopper 88. The directions of rotation are chosen such that as auger 90 rotates within hopper 88, any soil that is deposited in either end of hopper 88 will be drawn to the center. Auger pulley 92 is used to drive the rotation of auger 90 by a belt (not shown) as explained hereafter.

Disposed beneath auger 90 at a cut-out in the base of hopper 88 is spider wheel 94. The vanes of spider wheel 94 are formed such that as it rotates within its housing 96, soil that collects in the center portion of hopper 88 is drawn downward into housing 96. The vanes of spider wheel 94 form an air lock arrangement analogous to a revolving door, such that soil that is in the bottom portion of housing 96 is effectively sealed off from soil in hopper 88 above. The soil in the bottom portion of housing 96 may thus be pneumatically removed in a continuous fashion during operation.

Referring now to FIG. 11, compressed air is provided to housing 96 by means of air inlet 102. Air passing from inlet 102 to housing 96 forces soil that has collected in housing 96 by means of the rotation of spider wheel 94 to exit through air outlet 104. This soil is driven by means of air pressure to a collection point as described hereafter. The compressed air that passes into inlet 102 is received from rotary vane compressor 38, through an attached air hose (not shown).

Spider wheel 94 is mounted on a shaft as shown in FIG. 11, and driven by a flexible drive shaft (not shown) that is connected to a stub extending from a rear idler wheel 31. Drive pulley 106 on the spider wheel drive shaft drives auger pulley 92, as shown in FIG. 10, using two idlers (not shown) to turn the drive belt ninety degrees.

Referring again to FIGS. 5 and 6, the construction of guide assembly 108 according to a preferred embodiment of the invention may be described. The purpose of guide assembly 108 is to lead sampler assembly 60 along precise pathways as it travels with track 32, lowering and raising probe 66 and ejector 68 by means of manipulating the position of probe guide wheels 76 and ejector guide wheels 78 with respect to track 32. In addition, guide assembly 108 serves to securely hold sampler assembly 60 in position at certain key points as it revolves with track 32 by providing a track for base guide wheels 80. As a result, guide assembly 108 causes probe 66 and ejector 68 to automatically perform their intended functions at precise points along the rotation of sampler assembly 60 around track 32. In the preferred embodiment, guide assembly 108 is comprised of two sets of tracks, one disposed to the left side of drive mechanism 17 and the other to the right side of drive mechanism 17, such that each set of tracks provides support for the appropriate member of each pair of probe guide wheels 76, ejector guide wheels 78, and base guide wheels 80 on the corresponding side of sampler assembly 60. This arrangement is most clearly shown in FIG. 6. The space between these corresponding pairs of tracks must be open to allow sampler assembly 60 to pass therebetween. Further in the preferred embodiment, each set of tracks comprises a pair of lower base tracks 110, upper base tracks 112, lower probe tracks 114, upper probe tracks 116, lower ejector tracks 118, and upper ejector tracks 120. Each of these tracks may be attached to structural elements of drive mechanism 17 and thereby held rigidly in place as appropriate.

It should be noted that in the preferred embodiment, the various guide plates need not extend around the entire path of sampler assembly 60. Instead, guide plates are only needed at the points where alignment of sampler assembly 60 is critical, or where probe 66 or ejector 68 must be extended or retracted. Numerous other arrangements of guide plates could be employed in alternative embodiments, including a different number of guide plates, either more or less than the number used in the preferred embodiment. In addition, other forms of guide assembly 108 may be employed other than tracks, including without limitation in one alternative embodiment pairs of walled channels that trap one or more of probe guide wheels 76, ejector guide wheels 78, and base guide wheels 80 along part of or along the entire path followed by sampler assembly 60 as it follows track 32.

Referring now to FIGS. 12 and 13, the cycle by which soil sampling is performed as trailer 10 is moved across the ground according to a preferred embodiment of the present invention may now be described. At step A of FIG. 12, sampler assembly 60 has just revolved around front idler wheels 29. Because base guide wheels 80 are sandwiched between lower base track 110 and upper base track 112, base guide wheels 80 hold sampler assembly 60 rigidly in place, with the proper alignment of probe 66 toward the ground. It may be noted that in the preferred embodiment this alignment is near the vertical but angled slightly forward at about 12 degrees; in this way, probe 66 is perpendicular to track 32 at the point where probe 66 enters the ground, thereby minimizing the stress forces on probe 66 during insertion into the ground. Other alignments are, however, possible in alternative embodiments. It may further be seen that probe 66 is maintained in the fully retracted position, since lower probe track 114 and upper probe track 116 are holding probe guide wheels 76 at a relatively large distance from sampler base 62. Ejector 68 is collapsed fully within probe 66 at step A, because lower ejector track 118 is positioned so as to keep ejector guide wheels 80 relatively low with respect to sampler base 62. Thus in step A, scissor frame assembly is compressed at its upper section, but is extended in its lower section.

Moving now to step B of FIG. 12, it may be seen how the position of sampler assembly 60 changes as it continues its movement around the path of track 32. Lower base track 110 and upper base track 112 continue to hold sampler base 62 rigidly in place, maintaining the proper angle of probe 66 with respect to the ground. As sampler assembly 60 moves from step A to step B, however, lower probe track 114 and upper probe track 116 approach rubber track 32. As a result, probe guide wheels 65 are brought toward sampler base 62, the lower portion of scissor frame assembly 70 is compressed, and probe 66 extends into the ground. Simultaneously, since lower ejector track 118 is not approaching the ground, the distance between lower ejector track 118 on the one hand, and lower probe track 114 and upper probe track 116 on the other, is increasing. Thus ejector 68 is gradually retracted from within probe 66, and the upper portion of scissor frame assembly 70 is extended. The fact that ejector 68 withdraws from probe 66 as probe 66 is inserted into the ground allows soil to enter probe 66 through its open distal end. At step B of FIG. 12, probe 66 is fully extended into the soil, and ejector 68 is fully retracted from within probe 66. It may be noted that since track 32 is moving at precisely the speed of trailer 10 (because track 32 is driven by the motion of trailer 10 over the ground), the position of probe 66 with respect to the ground does not actually change during the movement from step A to step B. Thus probe 66 may be inserted directly into the ground as illustrated without lateral stress being exerted upon probe 66 by the soil immediately surrounding the point of insertion.

Moving now to step C of FIG. 12, it may be seen that lower base track 110 and upper base track 112 continue to hold sampler base 62 rigidly in place through the action of base guide wheels 80, maintaining the proper angle of probe 66 with respect to the ground. As sampler assembly 60 moves from step B to step C, however, lower probe track 114 begins to move upward and away from rubber track 32. As a result, probe guide wheels 65 are carried away from sampler base 62, the lower portion of scissor frame assembly 70 is extended, and probe 66 is retracted from the ground. Since lower ejector track 118 maintains an even distance with lower probe track 114 during the progression from step B to step C, ejector 68 maintains its fully withdrawn position with respect to probe 66. At step C of FIG. 12, probe 66 is fully retracted from the soil, and ejector 68 remains fully withdrawn from within probe 66. The friction of soil within probe 66 causes the soil to remain within probe 66, and since ejector 68 maintains its fully withdrawn position, there is no force acting to eject the soil from within probe 66.

Turning now to step D of FIG. 13, it may be seen that the distal end of probe 66 has now reached the lower end of hopper 88. Lower base track 110 and upper base track 112 continue to hold sampler base 62 in place, with the proper alignment of probe 66 maintained, as a result of base guide wheels 80. During the movement from step D to step E of FIG. 13, lower probe track 114 continues to rise while lower ejector track 118 assumes a flat trajectory. Also, the side of lower ejector track 118 above ejector guide wheels 78 is now so close to ejector guide wheels 78 that it may engage them from the top side, creating a narrow channel for ejector guide wheels 78. As a result, ejector guide wheels 78 begins to approach sampler base 62, the upper portion of scissor frame assembly 70 becomes compressed, and ejector 68 begins to compress within probe 66. At step E of FIG. 13, ejector 68 is fully extended within probe 66. The result of this progression from step D to step E is that as probe 66 passes over hopper 88, probe 66 remains retracted but ejector 68 continuously pushes soil out from probe 66 into hopper 88. By the time step E is reached, probe 66 is at the upper end of hopper 88, ejector 68 is at full compression within probe 66, and all of the soil within probe 66 has been deposited into hopper 88.

Turning now to step F of FIG. 13, it will be seen that lower probe track 114 rapidly approaches 32 in the progression from step E to step F. Simultaneously, lower ejector track 118 maintains its close position to lower probe track 114, with ejector guide wheels 78 remaining trapped between the portion of lower ejector track 118 beneath them and the portion of lower ejector track 118 that curves above them. As a result of these changes, probe 66 rapidly extends from sampler assembly 60, such that by the time step F is reached at the back of rear idler wheels 31 probe 66 is fully extended through track 32. Both the lower and upper portions of scissor assembly 70 are now fully compressed, since probe 66 is fully extended and ejector 68 is fully collapsed within probe 66. This position allows sampler assembly 60 to maneuver around the relatively tight turn at rear idler wheels 31. In addition, it will be noted that lower probe track 114 functions to hold sampler base 62 in the proper position for this turn through contact with base guide wheels 80. This position of sampler assembly 60 is maintained as sampler assembly 60 rotates to the position of step G of FIG. 13.

Turning now to step H of FIG. 13, it may be seen that lower probe track 114 gradually slopes away from track 32. This causes probe guide wheels 76 to be pulled away from sampler base 62, the lower portion of scissor frame assembly 70 extends, and probe 66 retracts within track 32. By the time that sampler assembly 60 reaches step H, probe 66 is in the fully retracted position. Since lower ejector track 118 also slopes away from track 32, and maintains an even distance between itself and lower probe track 114 between steps G and H, the position of ejector 68 with respect to sampler assembly 60 does not change. Thus the upper portion of scissor frame assembly 70 remains compressed, and ejector 68 remains fully compressed within probe 66.

Inertia due to the forward travel of rubber track 32 causes probe assembly 60 to hinge rearward; for this reason, strut 79 (shown in FIGS. 7 and 8) functions to hold the position of probe assembly 60 with respect to track 32 during parts of the probing cycle, particularly as probe assembly 60 passes rear idler wheels 31. It may be noted that there is no support for base guide wheels 80 at the upper portion of track 32 as provided by lower base track 110 and upper base track 112 at the lower portions of track 32; no such support is needed in the preferred embodiment since the angle of probe 66 and the precise alignment of sampler base 62 is not as critical during this portion of the probing cycle. Finally, it may also be noted that upper ejector track 120 provides an upper bound for the movement of ejector guide wheels 78 during portions of this cycle.

Turning now to FIGS. 14-15, the operation of a sampling bypass mechanism according to a preferred embodiment of the present invention may be described. It may occur that probe 66 strikes a rock or other hard object during a sampling cycle, and in such case it would be desirable to prevent damage to probe 66 by skipping the sampling operation during that particular cycle and maintaining probe 66 in a retracted position. Likewise, when large plots of grounds are covered for sampling, it may be desirable, for example, to sample only every second revolution of probe 66, third revolution of probe 66, or any other multiple of the number of revolutions. This may be accomplished through the manipulation of guide air cylinders 132. Guide air cylinders 132 are linked to the rearward portion of lower probe track 114 and upper probe guide extension 128, which may rotate about pivot point 130. Extension of each air cylinder 132, as shown in FIG. 15, allows the rearward portion of lower probe track 114 and upper probe guide extension 128 to pivot around pivot point 130 downwardly into the normal operating position. Air pressure within air cylinder 132 holds this position during normal sampling. If, however, probe 66 strikes an object that creates sufficient upward pressure on probe 66 to overcome the set air pressure in air cylinder 132, then air cylinder 132 may retract as shown in FIG. 14. The result of this retraction is the movement of probe 66 from the ground, and the sampling cycle will thereby be bypassed. In addition, air cylinder 132 may be retracted pneumatically for the purpose of skipping cycling samples as part of normal operations. The retraction and extension of air cylinder 132 may preferably be controlled by computer when used as part of the normal sampling operation. Air pressure for the operation of air cylinder 132 is provided by air tanks 23, shown in FIG. 4. Air from air tanks 23 is provided to air cylinder 132 by an air line (not shown for clarity). Air tanks 23 are thus used as a form of air bladder, allowing probe 66 to retract when an obstruction is encountered that is sufficiently resistive to the force of probe 66 to overcome the air pressure within air tanks 23.

Turning now to FIG. 10, that portion of the preferred embodiment of the invention that is concerned with sample collection may be described. Preferably, these components are located within reach of the operator, such as the driver of a tractor that is pulling trailer 10 during operation of the soil sampler. One possible arrangement is shown in FIG. 1, with the components located forward of the operator's position on vehicle 13. Soil delivery line 122 is used to pneumatically deliver each soil core from soil ejection hopper assembly 34 to soil collection canisters 126. Soil collection canisters are disposed upon carousel 125. While any number of collection canisters 126 may be employed, eight canisters are used in the preferred embodiment. The size of these canisters may vary, but in the preferred embodiment each canister 126 is sized to hold a plurality of soil cores. The rotation of carousel 125 is controlled by an onboard computer (not shown) that is in communication with control panel 124. Alternatively, control panel 124 may be a touchscreen display. This rotation may be accomplished by means of electric tray motor 134, as in the preferred embodiment, or by hydraulic, pneumatic, or other means. Electric tray motor 134 causes drive gear 136 to rotate, which in turn rotates secondary gear 138 attached to carousel 125. By rotating carousel 125, soil arriving through delivery line 122 may be deposited in any of canisters 126 as desired. This process may be controlled automatically in the preferred embodiment according to the method as described hereafter. This process may also be controlled, at the option of the operator, through a rotary switch positioned at control panel 124. Air exiting each canister 126 as air and soil arrive through delivery line 122 is filtered through a filter 140 attached to each canister 126; this prevents sample material from being inadvertently blown out of canister 126, and further prevents dust from canister 126 from causing discomfort to the operator, who is in the preferred embodiment positioned closely adjacent to canister 126.

In a preferred method according to the present invention, a grower may perform sampling over a field of interest utilizing mapping software and global positioning system (GPS) satellite information to highly automate the sampling process. For example, consider a square field of interest that of a size of 64 hectares. This field may be mapped using a GPS receiver and mapping software, with a tractor that simple travels the perimeter of the field. Such software is commercially available from companies such as Raven Industries of Sioux Falls, S.Dak., and Trimble Navigation Limited of Sunnyvale, Calif. The field may then be divided into, for example, sixty-four sections from which unique samples will be analyzed, using a grid that is overlaid by software onto the resulting field map. Each of the sampling sections will thus be of a size of 1 hectare.

In order to collect samples, the operator attaches trailer 10 to vehicle 13 and pulls trailer 10 to the edge of the field of interest. It may be noted that drive mechanism 17 should be raised during transport to the field of interest, since otherwise it will perform a sampling operation whenever trailer 10 is in motion. Vehicle 13 is then used to pull trailer 10 back and forth across the field, preferably crossing each grid section twice. Vehicle 13 may be manually guided by the operator, or the operator may take advantage of autosteer technology using GPS information, which is incorporated into many larger farm tractors now produced. Ground cores are periodically, and automatically, taken as the field is traversed. The GPS receiver of the tractor constantly monitors the location of trailer 10, and the onboard computer may be programmed to send a signal to electric tray motor 134 as each grid line is crossed. In this way, multiple cores are automatically taken from each sampling section, while the cores are deposited in a corresponding collection canister 126 without any further action by the operator. In the scenario described in the example hereof, it may be seen that since there are eight sampling sections of the field of interest in each row, and since there are eight canisters 126 on carousel 125, there is no need to empty the canisters for further collection until an entire row is completed. Preferably, carousel 125 and collection canisters 126 are disposed adjacent the operator so that the canisters 126 can be emptied into labeled packages without the requirement of the operator moving from his position with respect to vehicle 13. Thus sampling may be a continuous process over the entire field of interest, with sampling occurring automatically while the operator may empty canisters, mix collected samples if desired, and label the samples for later laboratory analysis. Alternatively, the system may include hardware to print a label that corresponds to each sampling area to further automate the sampling process. The label may include a barcode for machine reading. When sampling is complete, the operator may raise drive mechanism 17 with respect to tractor 10, and transport tractor 10 back to a storage area.

It should be noted that while the size of a field of interest and a sample area has been described with respect to the preferred embodiment, the invention may be employed in a field of any size, and sampling areas may be either increased or decreased in size based on the accuracy desired and the time in which the operator has available to perform the sampling operation. As described above, once the sections of the field of interest increase to a certain size, it may be preferable to only collect cores on every second revolution of probe 66, every third revolution of probe 66, or some other multiple of the number of revolutions. The inventor has found that roughly 100 cores are required to form a sample that has a mass of about 1 kg. Since the preferred sample size is around 0.25 kg, approximately 25 cores should be taken for each sample when using the preferred embodiment of the invention. Canisters 126 should preferably be sized so that they can easily receive at least this number of cores.

The present invention has been described with reference to certain preferred and alternative embodiments that are intended to be exemplary only and not limiting to the full scope of the present invention as set forth in the appended claims.

What is claimed is:

1. A soil sampling apparatus, comprising:
 (a) a frame;
 (b) a rotational drive member mounted to said frame;
 (c) a probe carriage attached to said rotational drive member;
 (d) a probe extendibly attached to said probe carriage; and
 (e) a guide comprising a probe track, wherein said probe rides within said probe track.

2. The soil sampling apparatus of claim 1, wherein said probe track extends toward said drive member from a first point on said guide toward a second point on said guide, and said probe track extends away from said drive member from said second point on said guide to a third point on said guide.

3. The soil sampling apparatus of claim 2, wherein said probe track extends toward said drive member from said third point on said guide to a fourth point on said guide.

4. The soil sampling apparatus of claim 3, further comprising an ejector attached to said probe carriage, wherein said guide further comprises an ejector track, and wherein said ejector rides within said ejector track.

5. The soil sampling apparatus of claim 4, wherein the distance between said probe track and said ejector track increases from said first point on said guide to said second point on said guide.

6. The soil sampling apparatus of claim 5, wherein the distance between said probe track and said ejector track decreases from said third point on said guide to said fourth point on said guide.

7. The soil sampling apparatus of claim 6, wherein said probe carriage comprises a first scissor member connecting said rotational drive member to said probe, and a second scissor member connecting said ejector to said first scissor member.

8. The soil sampling apparatus of claim 6, further comprising a rotational section of said probe track, and a compressible cylinder in communication with said rotational section of said probe track whereby said probe may be lifted by retraction of said compressible cylinder.

9. The soil sampling apparatus of claim 1, further comprising:

(a) a sample collection tray disposed to receive a soil sample from said probe;
(b) a sample container; and
(c) a pneumatic delivery system disposed between said sample collection tray and said sample container.

10. The soil sampling apparatus of claim 9, further comprising a sample tray in communication with said pneumatic delivery system, wherein said sample tray comprises a plurality of sample containers.

11. The soil sampling apparatus of claim 10, further comprising at least one auger at a base of said collection tray, and an air-lock delivery wheel beneath an aperture in the base of said collection tray in communication with said pneumatic delivery system.

12. The soil sampling apparatus of claim 10, further comprising an electronic control system operable to deposit a sample in one of said plurality of sample containers based upon the location of the soil sampling apparatus with respect to a field of interest.

13. The soil sampling apparatus of claim 12, wherein said electronic control system comprises a GPS receiver.

* * * * *